United States Patent [19]

Baudouin et al.

[11] Patent Number: 5,030,769

[45] Date of Patent: Jul. 9, 1991

[54] CONTINUOUS DIRECT PREPARATION OF NITROPHENOLS

[75] Inventors: Michel Baudouin, Craponne; Jean-Luc Bougeois, Sainte Foy Les Lyon; Serge Ratton, Villefontaine; Jean-Pierre Lecouve, Caluire, all of France

[73] Assignee: Rhone-Poulenc Chimie, Courbevoie, France

[21] Appl. No.: 432,498

[22] Filed: Nov. 7, 1989

[30] Foreign Application Priority Data

Nov. 7, 1988 [FR] France ............................... 88 15185

[51] Int. Cl.[5] ................... C07C 205/20; C07C 205/21
[52] U.S. Cl. .................................................... 568/706
[58] Field of Search ................................. 568/706, 710

[56] References Cited

U.S. PATENT DOCUMENTS 3,980,717  9/1976  Subluskey ........................... 568/706
4,112,005  9/1978  Thiem et al. ........................ 568/706

FOREIGN PATENT DOCUMENTS 0211775  2/1987  European Pat. Off.
2144395  2/1973  France ................................ 568/706
1098717  10/1968  United Kingdom ................ 568/706

Primary Examiner—Werren B. Lone
Attorney, Agent, or Firm—Burns, Doane, Swecker and Mathis

[57] ABSTRACT

Nitrophenols, in an isomer ratio para-nitrophenol/ortho-nitrophenol of at least 55/45, are continuously and directly prepared in steady state, by (a) establishing, in a confined reaction zone, an aqueous reaction solution including from 5% to 40% by weight of nitric acid, from 5% to 40% by weight of nitrous acid relative thereto, and an amount of nitrophenols within the limits of the solubility thereof in such reaction solution, (b) continuously introducing and reacting phenol and nitric acid into and with such reaction solution, at a rate of about 0.5 to 2.0 moles of nitric acid per mole of phenol, (c) maintaining the temperature in such confined reaction zone at a value ranging from about 10° to about 40° C. during such reaction, and (d) continuously withdrawing from such confined reaction zone admixture of para-nitrophenol and ortho-nitrophenol, in an isomer ratio para-nitrophenol/ortho-nitrophenol of at least 55/45.

13 Claims, 1 Drawing Sheet

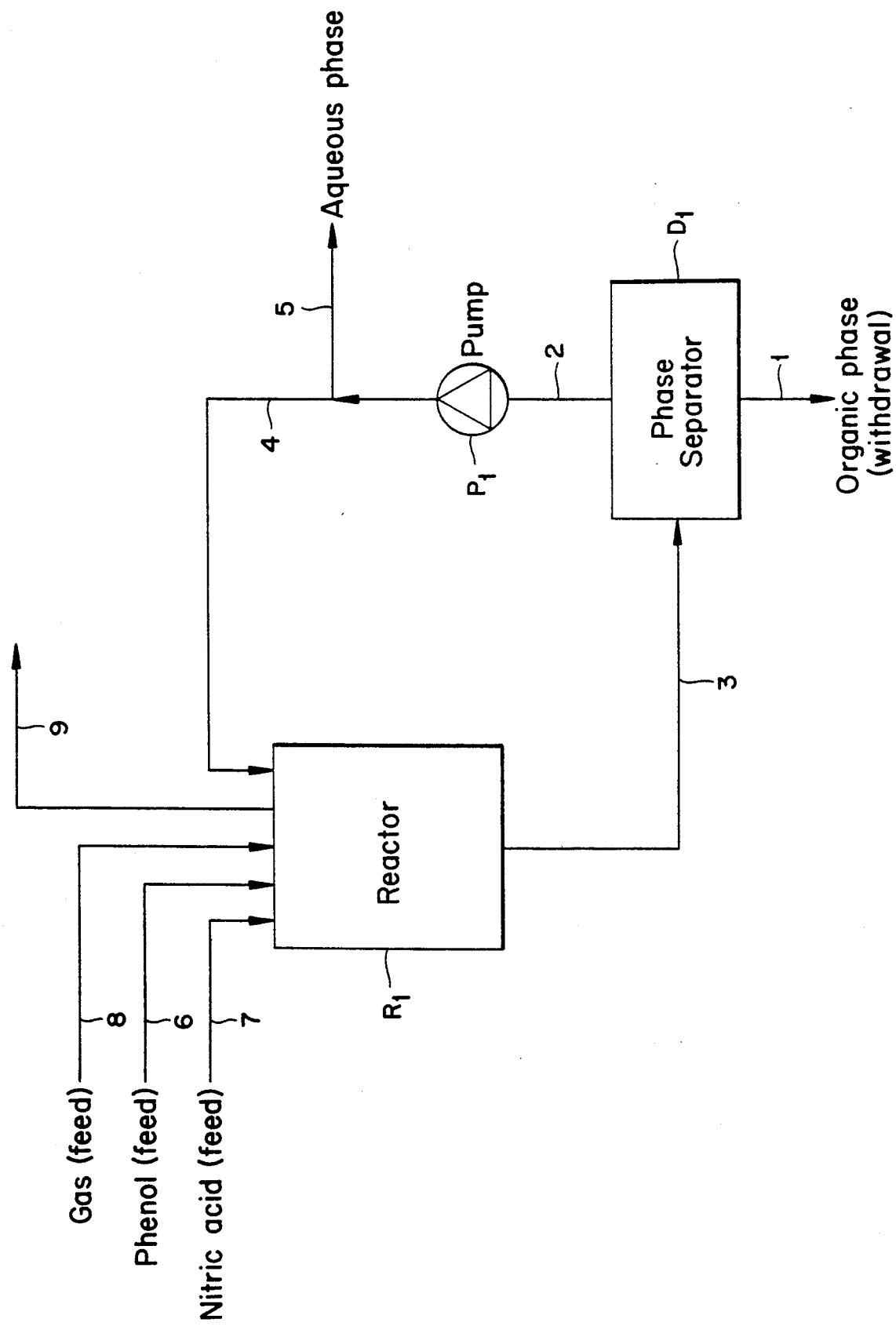

CONTINUOUS DIRECT PREPARATION OF NITROPHENOLS

BACKGROUND OF THE INVENTION

1. Field of the Invention

The present invention relates to a continuous process for the preparation of nitrophenols and, more especially, to the continuous preparation of nitrophenols by nitrating phenol in an aqueous medium.

2. Description of the Prior Art

The nitration of phenol is a reaction which has long been known to this art. Numerous publications exist on this subject and very frequently they are divergent with regard to the mechanism of the reaction or, more precisely, of the competing reactions (nitration, nitrosation, oxidation, dinitration and polycondensation). One of the basic problems that is encountered when phenol is nitrated is that of the selectivity of the nitration. Indeed, direct nitration of phenol produces an ortho-nitrophenol/para-nitrophenol ratio which is substantially 50/50. However, industrial demand for ortho-nitrophenol is much less than that for para-nitrophenol. As a result of this, to satisfy the industrial requirements for para-nitrophenol, ortho-nitrophenol is produced in quantities greatly in excess of the demand therefor.

Various solutions to the above problem have been proposed in order to promote production of the para derivative, or even for obtaining only the para derivative. It has for example been proposed to prepare para-nitrosophenol, first by nitrosation with the aid of nitrous acid, and then oxidizing the para-nitrosophenol to para-nitrophenol. Such a process is, economically, relatively unprofitable. Furthermore, nitrosophenol is an unstable compound which presents thermal explosion hazards. Therefore, it is preferable not to accumulate this compound in large quantities.

Patent GB 1,098,717 describes the nitration of phenol with nitric acid in aqueous medium, in the presence of nitrous acid and sulfuric acid, with specified concentrations of these various acids, especially high concentrations of sulfuric acid. According to the alternative embodiment of such process, there is either a precipitation of solids in the reactor, or, in order to avoid such precipitation, a very slow rate of introduction of the phenol. From an industrial standpoint, such a process presents major technical problems (high concentration of sulfuric acid, precipitation of a solid, low production efficiency).

To overcome these disadvantages, FR 2,144,395 describes a process entailing reacting phenol or derivative thereof in an aqueous mixture of nitric acid and nitrous acid at a temperature of −15° C. to +15° C., while maintaining a certain concentration of nitric acid and an overall nitric acid/phenol molar ratio of 4/1 to 5/1.

This process produces a pasty reaction mixture, which is heated upon completion of the addition of phenol in order to dissolve the solids or suspension. Therefore, it is indeed a two-step process, which is difficult to implement continuously on an industrial scale.

SUMMARY OF THE INVENTION

Accordingly, a major object of the present invention is the provision of an improved continuous process for the direct nitration of phenol to nitrophenols, and wherein the reaction product displays a para-nitrophenol/ortho-nitrophenol ratio higher than or equal to 55/45.

Briefly, the present invention features a steady state continuous process for the preparation of nitrophenols in aqueous medium, comprising (a) continuously introducing phenol and nitric acid, at a rate of approximately 0.5 to 2.0 moles of nitric acid per mole of phenol, into a closed stirred reactor containing a reaction mixture consisting essentially of an aqueous solution which comprises from 5% to 40% by weight of nitric acid, nitrous acid in a proportion of 5% to 40% by weight relative to the weight of the nitric acid, and nitrophenols within the limit of their solubility in such medium, (b) maintaining the temperature in the reactor at from about 10° C. to about 40° C., and (c) continuously withdrawing from the reactor a mixture consisting essentially of para-nitrophenol and ortho-nitrophenol with a para-nitrophenol/ortho-nitrophenol isomer ratio higher than or equal to 55/45.

BRIEF DESCRIPTION OF THE DRAWING

The FIGURE of Drawing is a schematic/diagrammatic illustration of process/apparatus for carrying out the continuous direct nitration according to the invention.

DETAILED DESCRIPTION OF THE PREFERRED EMBODIMENTS OF THE INVENTION

More particularly according to the present invention, the concentration of the nitric acid in the aqueous solution of the reaction mixture preferably ranges from 10% to 25% on a weight-to-weight basis The nitrous acid/nitric acid weight ratio in the aqueous layer of the reaction mixture preferably ranges from 10% to 20%. The temperature of the reaction mixture preferably is maintained from about 15° C. to about 30° C.

The phenol is generally introduced in liquid form. It may therefore be introduced either in the molten state or may be introduced as a mixture with water. In this latter case, mixtures comprising from 70% to 90% by weight of phenol are suitable. Although water/phenol mixtures containing less than 70% by weight of phenol can be employed, this is hardly advantageous on an industrial scale, because it will be necessary to prevent this water from accumulating and, hence, to provide a system for extracting the excess water from the reaction environment.

The nitric acid can also be introduced in the pure state or in the form of an aqueous solution.

For the same reason as given above, the introduction of pure nitric acid makes it possible to avoid introducing water. On the other hand, for economic reasons, it may be preferable to employ commercial aqueous solutions of nitric acid, such as, for example, the solution containing approximately 68% of nitric acid, which corresponds to the water/nitric acid azeotropic mixture.

The mixture of nitrophenols which is formed separates out in the form of an oily liquid in the lower, unstirred section of the reactor, or in a second unit used as a phase separator and connected to and communicating with the lower section of the reactor.

This mixture, consisting essentially of mononitrophenols, also contains water, a minor amount of dissolved nitric acid, together with by-products of the reaction, such as dinitrophenols and benzoquinone.

If the amount of water which is removed in this manner is smaller than the amount of water formed by the nitration reaction on the one hand, and possibly introduced with the phenol and the nitric acid on the other, such excess water must be removed at regular intervals.

To accomplish this, a fraction of the aqueous layer present in the reactor can, for example, be removed when thought necessary.

This withdrawn portion of aqueous layer may be concentrated to remove the desired amount of water therefrom and may then be recycled into the reactor.

It may also be carried out in such a manner that this corresponds to the amount of water which must be removed and, in this case, there is no recycling of this withdrawn fraction, the loss of nitric acid being then compensated for by adjusting the amount of nitric acid which is continuously introduced.

The molar ratio of nitric acid and of the phenol which are continuously introduced will be adjusted as a function of the desired degree of conversion of the phenol and of the recycling or absence of recycling of the withdrawn fractions of the aqueous layer of the reaction mixture, after the said withdrawn fractions have been treated and/or concentrated. When the latter are recycled, the loss of nitric acid is less great and a nitric acid/phenol molar ratio of 0.9 to 1.5 is generally suitable.

The pressure in the reactor is the autogenous pressure of the various reactants and products formed.

It is generally maintained at a value ranging from 0.1 MPa (1 bar) to 1 MPa (10 bars) absolute.

While this is generally not the case, it is also within the ambit of the invention to carry out the process while maintaining an absolute pressure of less than 0.1 MPa in the reactor.

Because of the formation of gaseous by-products, the pressure in the reactor must be adjusted to the selected value either at regular intervals or continuously by means of a degassing system which is functional as soon as the selected value of reactor pressure is attained.

The gases which constitute the overhead phase of the reactor and part of which is thus removed, consist essentially of carbon dioxide and of various nitrogen oxides, the quantitatively most abundant of which is NO.

The autogenous pressure in the reactor is preferably maintained at a value ranging from 0.1 MPa to 0.5 MPa absolute.

Since the process according to the invention is continuously carried out and generates by-products, the latter are essentially withdrawn with the nitrophenols. However, some may be partially soluble in the aqueous phase which remains in the reactor. A certain progressive accumulation of such by-products may therefore take place in the reactor.

To ensure that the process is properly carried out, it is easy to provide a purge of the aqueous layer containing nitric and nitrous acids at regular intervals. This purge may include a withdrawn fraction of the aqueous layer and a treatment of such withdrawn fraction entailing oxidizing the by-products to carbon dioxide and water, using the nitric acid present. This may be carried out, for example, by heating the withdrawn fraction in an adjoining unit and then, after removing the by-products, by reintroducing the treated solution into the reactor.

It will of course be appreciated that the removal of any excess of water from the reaction mixture can be combined with the removal of the by-products, for example by heating the withdrawn fraction of the aqueous layer beforehand to oxidize the by-products and then distilling off the excess water before reintroducing the purified and concentrated withdrawn material into the reactor.

The process according to the invention has many advantages. There is practically no detectable nitrosophenol in the nitration reactor, in contrast to the nitrosation/oxidation processes of the prior art. The hazards associated with the accumulation of such compound are therefore eliminated.

The reaction takes place in one stage and not in two stages: nitrosation followed by an oxidation of nitrosophenol to nitrophenol. The reaction mixture is liquid and consists essentially of the aqueous phase in which the nitration reaction takes place and the mixture of the nitrophenols produced, which separates out in the lower section of the reactor or in a phase separator, and which is continuously withdrawn therefrom.

The process is also very simple, since it is sufficient, for example, to modify the temperature in the reactor to obtain, as needed, a more or less high para-nitrophenol/ortho-nitrophenol ratio. As a general rule, the increase in temperature lowers the para-nitrophenol-ortho-nitrophenol ratio, all other factors being equal.

Finally, in contrast to the processes of the prior art, there is no need to add nitrous acid or one of its precursors (such as NO of $NO_2$) when the process is in a steady state: only phenol and nitric acid are continuously charged. The role played by the nitrous acid is in fact only that of a catalyst.

The process according to the invention can be advanced to a steady state in various ways.

An aqueous solution of nitric acid at a concentration of 5% to 40% by weight can be introduced into the reactor and then, after a temperature of 10° C. to 40° C. has been established, the nitration can be commenced by introducing the phenol and the nitric acid continuously, in a phenol/nitric acid molar ratio of 0.5 to 2.

For a certain time period, which will be referred to as the induction period, the para-nitrophenol/ortho-nitrophenol isomer ratio of the nitrophenol mixture which is withdrawn will be substantially 50/50. After this induction period, of a few minutes to approximately a few hours, the process will be in a steady state and the para-nitrophenol/ortho-nitrophenol ratio will be higher than or equal to 55/45, particularly depending on the temperature which is adopted.

This induction period may also be completely eliminated by introducing into the reactor, at process start-up and only at this time, nitrous acid or precursor thereof, namely, either nitrous acid or an alkali metal nitrite such as sodium nitrite, or a pressure of 0.1 MPa to 0.5 MPa of NO, or both nitrous acid and one of its precursors.

The apparatus in which the process of the invention may be carried out advantageously comprises:

(i) a reactor equipped with means for stirring and for heating and cooling, and outlet means for withdrawing a portion of final product from the lower section thereof;

(ii) inlet means for introducing the reactants: phenol and nitric acid;

(iii) means for degassing and regulating pressure; and (iv) means for withdrawing a fraction of the aqueous layer for purging and for reintroducing, if appropriate, the said withdrawn fraction after appropriate treatment thereof.

The reactor may also comprise two units:

(1) the reactor proper, where the reaction is carried out and where the level of the reaction mixture is maintained constant; and (2) a phase separator in which the aqueous reaction phase, which is continually recycled, and the nitrophenol phase, which is withdrawn, are continuously separated.

The treatment of the nitrophenol mixture is carried out by any conventional means, such as distillation, steam distillation and recrystallization.

In order to further illustrate the present invention and the advantages thereof, the following specific examples are given, it being understood that same are intended only as illustrative and in nowise limitative.

EXAMPLE 1

Description of the apparatus

The apparatus employed comprised (see attached single FIGURE of Drawing):

(i) a cylindrical glass reactor $R_1$ having a working volume of 1 liter, stirred by means of a turbine; this apparatus could be cooled by circulating water through a jacket;

(ii) a phase separator $D_1$ including a horizontal glass cylinder having a capacity of 0.16 liters provided with a base outlet 1 and a top outlet 2;

(iii) a pump device $P_1$ and appropriate conduits permitting the phase separator to be continuously charged with the liquid content 3 from the reactor and the upper liquid layer 4 to be returned, after phase separation, from the phase separator to the reactor, or as liquid 5 exiting to a purge device.

The reactor was also equipped with inlet means for continuously introducing an aqueous phenol solution, via line 6, on the one hand, and an aqueous nitric acid solution, via line 7, on the other. Lastly, it included means permitting gases to be introduced, via line 8, and released, via line 9, at atmospheric pressure.

Operation of the continuous reaction

Initial charges

The reactor $R_1$ and the phase separator $D_1$ were charged with 901.5 g of an aqueous solution containing 2.810 moles of nitric acid and 0.379 moles of nitrous acid. This mixture was prepared initially by absorbing nitric oxide, NO, in a dilute aqueous solution of nitric acid.

The mixture was stirred and maintained at a temperature of 25° C. and circulated continuously from the phase separator $D_1$ to the reactor $R_1$, by means of the pump $P_1$, at a rate of 7 liters/hour.

Continuous operation of the reaction

The following materials were continuously charged into the reactor $R_1$:

(i) 117.1 g/hour of an $HNO_3$/water mixture containing 68% of $HNO_3$; and (ii) 114.8 g/hour of a phenol/water mixture containing 80.4% of phenol.

The reactor contents were maintained at 25° C. by circulating cold water through the jacket.

After 35 minutes of operation, the reaction mixture separated into two liquid phases:

(a) a lower organic phase principally comprising nitrophenols; and (b) an upper organic phase containing $HNO_3$, $HNO_2$ and saturated with nitrophenols.

The separated organic phase was withdrawn from the base of the phase separator $D_1$ (1), while the aqueous phase was returned via $P_1$ into the reactor $R_1$ (4).

The combined liquid volume content of the reactor and of the phase separator was maintained constant by continuously withdrawing a fraction of the aqueous phase from the delivery of the pump $P_1$ (5).

The gases produced by the reaction, essentially $CO_2$ and NO, were discharged merely by release thereof at atmospheric pressure (9).

The composition of the organic phase and of the aqueous phase which were continuously withdrawn was determined by liquid phase chromatography and also by potentiometry.

Samples of the aqueous phase, taken every 3 hours, were clarified by centrifugation and were analyzed. Table No. 1 reports the change in the composition over time.

The organic phase withdrawn from the phase separator $D_1$ (1), collected every 3 hours, was weighed and analyzed. The mass and the composition of each fraction are reported in Table No. 2.

The aqueous phase separated off and withdrawn from the unit throughout the experiment (12 hours) represented a mass of 978.6 g. A constant release (9) of a total amount of 39.4 liters of gas (measured at 25° C. and atmospheric pressure) was observed at the outlet of the reactor $R_1$. This gas contained 49% by volume of nitric oxide, NO.

The overall balance of the experiment, after 12 hours of operation, evidenced that 11.77 moles of phenol were consumed and that the following were recovered:

(1) 0.084 moles of phenol (degree of conversion 99.3%);

(2) 6.886 moles of para-nitrophenol (CY* = 58.9%);

(3) 3.525 moles of ortho-nitrophenol (CY* = 30.2%);

* CY : yield based on the phenol converted.

TABLE No. 1

| COMPOSITION OF THE AQUEOUS PHASE: | | | | | |
|---|---|---|---|---|---|
| | Time in hours | | | | |
| Concentration | 0 | 3 | 6 | 9 | 12 |
| $HNO_3$ mole/kg | 3.117 | 2.433 | 2.419 | 2.317 | 2.346 |
| $HNO_2$ mole/kg | 0.420 | 0.276 | 0.281 | 0.312 | 0.264 |
| p-Nitrophenol mole/kg | 0 | 0.298 | 0.260 | 0.257 | 0.250 |
| o-Nitrophenol mole/kg | 0 | 0.071 | 0.040 | 0.037 | 0.036 |

TABLE No. 2

| ORGANIC PHASE WITHDRAWN: | | | | |
|---|---|---|---|---|
| Fraction | 1 | 2 | 3 | 4 |
| Production period | 0 to 3 h | 3 h to 6 h | 6 h to 9 h | 9 h to 12 h |
| Mass (g) | 285.7 | 421 | 439 | 441 |
| p-Nitrophenol % by weight | 51.4 | 52.4 | 53.5 | 56.7 |
| o-Nitrophenol % by weight | 34.0 | 28.6 | 27.4 | 28.2 |
| Phenol % by weight | not determined | 0.16 | 0.17 | 0.17 |
| Benzoquinone % by weight | 1.07 | 0.67 | 1.16 | 0.96 |
| Dinitrophenols % by weight | 1.1 | 0.57 | 0.39 | 0.32 |
| Water % by weight | 11.1 | 11.8 | 11.8 | 11.8 |

EXAMPLE 2

The experiment was carried out in the apparatus described in Example No. 1.

Initial charge

The reactor $R_1$ and the phase separator $D_1$ were charged with 915 g of an aqueous solution containing 2.956 moles of nitric acid. (No nitrous acid).

Reaction

Induction stage

The mixture was stirred and maintained at a temperature of 28° C. It circulated continuously from the phase separator $D_1$ to the reactor $R_1$ by means of the pump $P_1$, at a rate of 8 liters/hour.

69 grams of a phenol/water mixture containing 80.5% of phenol were added continuously at a constant rate to the reactor $R_1$; the period of introduction was 44 min; the temperature of the mixture present in the reactor $R_1$ was maintained at 28° C. by circulating cold water through the jacket.

The addition of phenol was then terminated for 37 min and the temperature of 28° C. was maintained during this period.

Continuous operation of the reaction

Beginning from the induction phase described above, the following materials were continuously charged into the reactor $R_1$:

(i) 118.5 g/h of an $HNO_3$/water mixture containing 68% of $HNO_3$;

(ii) 118.5 g/h of a phenol/water mixture containing 80.5% of phenol.

The organic phase separated off was withdrawn continuously from the base of the phase separator $D_1$ (1) while the aqueous phase was returned via $P_1$ into the reactor $R_1$ (4).

The combined liquid volume content of the reactor and of the phase separator was maintained constant by continuously withdrawing a fraction of the aqueous phase from the delivery of the pump $P_1$ (5).

The gases produced by the reaction were discharged from the reactor such as to maintain a constant internal pressure equal to atmospheric pressure (9).

During the initial period of 45 minutes, the temperature of the reaction mixture was progressively reduced from 28° C. to 25° C. and it was then maintained at this latter value for another 7 h, 15 min.

Samples taken at various times from the aqueous phase and from the organic phase were analyzed (Tables No. 3 and 4).

A material balance performed while the reaction was continuously operated for 4 h, 11 min, evidenced that 4.252 moles of phenol were consumed and that the following were recovered:

(a) 0.015 moles of phenol (degree of conversion 99.6%);

(b) 2.503 moles of para-nitrophenol (CY*=59.1%);

(c) 1.163 moles of ortho-nitrophenol (CY*=27.5%).

* CY=yield based on the phenol converted.

TABLE No. 3

| COMPOSITION OF THE AQUEOUS PHASE: | | | | | |
|---|---|---|---|---|---|
| | Time in hours | | | | |
| Concentration | 1 | 2 | 4 | 6 | 8 |
| $HNO_3$ mole/kg | 2.417 | 2.113 | 2.171 | 2.211 | 2.230 |
| $HNO_2$ mole/kg | 0.114 | 0.201 | 0.196 | 0.223 | 0.205 |
| p-Nitrophenol mole/kg | 0.207 | 0.144 | 0.229 | 0.232 | 0.234 |
| o-Nitrophenol mole/kg | 0.036 | 0.023 | 0.033 | 0.034 | 0.036 |

*From the beginning of the continuous operation of the reaction.

TABLE No. 4

| COMPOSITION OF THE ORGANIC PHASE: | | | | | |
|---|---|---|---|---|---|
| | Time in hours | | | | |
| Concentration | 1 | 2 | 4 | 6 | 8 |
| p-Nitrophenol % by weight | 50.8 | 52.3 | 52.7 | 52.7 | 53.5 |
| o-Nitrophenol % by weight | 31.5 | 26.6 | 24.9 | 24.9 | 25.3 |
| Phenol % by weight | 0.09 | 0.12 | 0.11 | 0.08 | 0.22 |
| Benzoquinone % by weight | 2.5 | 2.1 | 1.8 | 1.8 | 1.9 |
| Dinitrophenols % by weight | 0.21 | 0.15 | 0.15 | 0.14 | 0.15 |

*From the beginning of the continuous operation of the reaction.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A process for the continuous direct preparation of nitrophenols in steady state, comprising (a) establishing, in a confined reaction zone, an aqueous reaction solution which comprises from 5% to 40% by weight of nitric acid, from 5% to 40% by weight of nitrous acid relative thereto, and an amount of nitrophenols within the limits of the solubility thereof in such reaction solution, (b) continuously introducing and reacting phenol and nitric acid into and with such reaction solution, at a rate of about 0.5 to 2.0 moles of nitric acid per mole of phenol, (c) maintaining the temperature in said confined reaction zone at a value ranging from about 10° to about 40° C. during such reaction, and (d) continuously withdrawing from said confined reaction zone admixture of para-nitrophenol and ortho-nitrophenol, in an isomer ratio para-nitrophenol/ortho-nitrophenol of at least 55/45.

2. The process as defined by claim 1, said aqueous reaction solution being confined in a closed stirred reactor.

3. The process as defined by claim 2, wherein the autogenous pressure in said reactor ranges from 0.1 MPa to 1 MPa.

4. The process as defined by claim 3, said pressure ranging from 0.1 MPa to 0.5 MPa.

5. The process as defined by claim 1, wherein the concentration of nitric acid in an aqueous layer of such reaction mixture ranges from 10% to 25% by weight.

6. The process as defined by claim 5, wherein the nitrous acid/nitric acid weight ratio in an aqueous layer of such reaction mixture ranges from 10% to 20%.

7. The process as defined by claim 6, wherein the temperature of the reaction mixture is maintained from about 15° C. to about 30° C.

8. The process as defined by claim 1, wherein the molar ratio of nitric acid to the phenol continuously introduced ranges from 0.9 to 1.5.

9. The process as defined by claim 1, said phenol being continuously introduced in molten state.

10. The process as defined by claim 1, said phenol being continuously introduced in admixture with water.

11. The process as defined by claim 1, said nitric acid being continuously introduced as an aqueous solution thereof.

12. The process as defined by claim 1, comprising recycling water from said final product admixture to said confined reaction zone.

13. The product of the process as defined by claim 1.

* * * * *